(12) United States Patent
Albarracin et al.

(10) Patent No.: US 12,171,189 B2
(45) Date of Patent: Dec. 24, 2024

(54) ABSORBENT PAD WITH DRAWSTRING SYSTEM AND METHOD

(71) Applicants: Eddie Albarracin, Scottsdale, AZ (US); Gretchen Zamjahn, Scottsdale, AZ (US)

(72) Inventors: Eddie Albarracin, Scottsdale, AZ (US); Gretchen Zamjahn, Scottsdale, AZ (US)

(73) Assignee: Mr. PeePad LLC, Wilmington, DE (US)

( * ) Notice: Subject to any disclaimer, the term of this patent is extended or adjusted under 35 U.S.C. 154(b) by 199 days.

(21) Appl. No.: 17/740,384

(22) Filed: May 10, 2022

(65) Prior Publication Data

US 2023/0363349 A1 Nov. 16, 2023

(51) Int. Cl.
| | |
|---|---|
| *A01K 1/015* | (2006.01) |
| *A61F 5/48* | (2006.01) |
| *A61F 13/551* | (2006.01) |
| *A61F 13/15* | (2006.01) |

(52) U.S. Cl.
CPC ............ *A01K 1/0157* (2013.01); *A61F 5/485* (2013.01); *A61F 13/551* (2013.01); *A61F 2013/15154* (2013.01); *A61F 2013/15186* (2013.01); *A61F 2013/55195* (2013.01)

(58) Field of Classification Search
CPC .... A01K 1/0157; A01K 23/00; A01K 23/005; A61F 5/485; A61F 13/64; A61F 13/551; A61F 2013/15048; A61F 2013/15056; A61F 2013/15073; A61F 2013/15154; A61F 2013/15186; A61F 2013/55195
See application file for complete search history.

(56) References Cited

U.S. PATENT DOCUMENTS

| | | | | |
|---|---|---|---|---|
| 3,626,900 | A * | 12/1971 | Failla | A01K 1/0107 |
| | | | | 119/161 |
| 7,249,570 | B1 * | 7/2007 | Roberson | A01K 1/0157 |
| | | | | 119/169 |
| 8,960,127 | B2 * | 2/2015 | Miller | A01K 23/005 |
| | | | | 119/169 |
| 9,357,746 | B2 * | 6/2016 | Miller | A01K 1/0125 |
| 9,445,575 | B2 * | 9/2016 | Ferguson | A01K 1/0157 |
| 9,681,640 | B2 | 6/2017 | Miller | |
| 10,568,299 | B2 * | 2/2020 | Miller | B32B 27/12 |
| 10,851,505 | B2 * | 12/2020 | Morancie-Davidson | |
| | | | | E01H 1/1206 |
| 11,129,365 | B1 * | 9/2021 | Gregson | A01K 1/0107 |
| 11,452,278 | B1 * | 9/2022 | Nelson | A01K 1/0107 |
| 2003/0005891 | A1 * | 1/2003 | Lu | A01K 1/0107 |
| | | | | 119/867 |
| 2009/0114161 | A1 * | 5/2009 | Carnahan | A01K 1/0125 |
| | | | | 119/169 |

(Continued)

*Primary Examiner* — Catharine L Anderson
(74) *Attorney, Agent, or Firm* — Invention To Patent Services; Alex Hobson

(57) ABSTRACT

An absorbent pad with drawstring system; the absorbent pad with drawstring system includes an absorbent pad having a drawstring system and a planar body with multiple layers configured to absorb liquid-waste and collect solid-waste. The absorbent pad with drawstring system is provided for use in both professional environments and private households for collecting solid-waste and liquid-waste for sanitary containment and disposal of the solid-waste and the liquid-waste.

2 Claims, 9 Drawing Sheets

(56) References Cited

U.S. PATENT DOCUMENTS

2014/0338606 A1* 11/2014 Takagi ................. A01K 1/0157
119/161
2019/0343080 A1* 11/2019 Chapman ............. A01K 23/005

* cited by examiner

ABSORBENT PAD WITH DRAWSTRING SYSTEM AND METHOD

CROSS-REFERENCE TO RELATED APPLICATION(S)

The present application is related to and claims priority to U.S. Provisional Patent Application No. 63/361,127 filed Nov. 29, 2021, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of pads of existing art and more specifically relates to pads with drawstrings.

RELATED ART

Absorbent pads are used in a variety of scenarios including medical settings and home settings. Absorbent pads are often applied to examination tables and beds such as for particular in-office treatments and outpatient procedures. The absorbent pads may be used to catch and absorb bodily fluids including blood, saliva, blister serum, mucus, pus, urine, fecal matter and other bodily fluids that may be secreted. These bodily fluids may contain countless germs, bacteria and even pathogens.

In recent times, pet waste pads were developed, which are similar to the absorbent pads described above, to attract pets and, in particular, dogs and/or puppies to an area, so said dogs and/or puppies may defecate and/or urinate on said pet waste pads, in order to minimize deposits of such waste in undesired parts of the living quarters. The pet waste pads can then be picked up with the excrement thereon. However, to this day, disposal of such deposits of fecal matter and/or urine remains unsanitary, unhygienic, and potentially pathogenically harmful. In many such instances, the human guardians may come into contact with such exposed excrement and/or urine, either from spilling such wastes or touching such wastes during carrying and/or disposal of the pet waste pads. A suitable sanitary means for disposal of various solid and liquid waste is desired.

U.S. Pat. No. 8,960,127 to Martin Miller relates to a waste pad. The described waste pad includes a pet waste collection apparatus having a drawstring within an outer peripheral border of the pet waste collection apparatus, the drawstring having a drawstring exit portion exiting the pet waste collection apparatus, the drawstring exit portion of the drawstring releasably fastened to a bottom corner portion of the pet waste collection apparatus, the pet waste collection apparatus adapted to form a shape of a bag when the drawstring exit portion of the drawstring is released from the bottom corner portion of the pet waste collection apparatus and the drawstring is pulled taut, the pet waste collection apparatus substantially enclosing and sealing pet waste within the pet waste collection apparatus when the drawstring is pulled taut. Alternative embodiments include a bifurcated exit sleeve, an alternate exit sleeve, and a tab, each adapted to adhesively and releasably fasten the drawstring exit portion to the bottom corner, and a leak protection barrier.

SUMMARY OF THE INVENTION

In view of the foregoing disadvantages inherent in the known pads art, the present disclosure provides a novel absorbent pad with drawstring system. The general purpose of the present disclosure, which will be described subsequently in greater detail, is to provide an absorbent pad with drawstring system that makes picking up and disposing of a soiled pad easier, quicker, safer and more sanitary.

An absorbent pad with drawstring system is disclosed herein. The absorbent pad with drawstring system may include an absorbent pad having a drawstring. The absorbent pad with drawstring system may comprise a generally square or rectangular profile. The planar body includes an absorbent pad produced with super absorbent polymer (SAP) as a base material, along with supporting pulp and tissue. Said absorbent pad includes a hydrophilic lining and the hydrophobic lining, as well. The hydrophilic lining is on the top-exterior plane of the absorbent pad. The hydrophobic lining is included on the bottom-interior plane of the absorbent pad. The absorbent pad is centered and secured upon a base liner. An adhesive section is positioned on the exterior bottom of the base liner of the absorbent pad for securing and maintaining placement of the absorbent pad on a hosting surface. The base liner preferably comprises a plastic, waterproof material. The absorbent pad is provided for collecting solid-waste and liquid-waste for sanitary containment and disposal of the solid-waste and the liquid-waste. The absorbent pad with drawstring system prevents germs, bacteria, and pathogens present in its collected waste from escaping to other areas in its environment of use. By preventing escape of germs, bacteria, and pathogens, the absorbent pad with drawstring system prevents said germs, bacteria, and pathogens from contacting other objects and persons in an environment of use.

According to a first embodiment, the absorbent pad with drawstring system is provided for medical use. The absorbent pad with drawstring system collects discharges from the body, such as but not limited to urine, feces, blood, saliva, perspiration and pus. According to a second embodiment, the absorbent pad with drawstring system is provided for pet use. The absorbent pad with drawstring system may comprise a generally square or rectangular profile. The absorbent pad comprises a plurality of layers. The planar body includes the hydrophilic lining and the hydrophobic lining. The hydrophilic lining is on the top-exterior plane of the absorbent pad. The absorbent pad includes super absorbent polymer (SAP) as a base material, along with supporting pulp and tissue. The hydrophobic lining is included on the bottom-interior plane of the absorbent pad. The absorbent pad is centered on the base liner. The base liner preferably extends past a perimeter border of the absorbent pad and folds back on to the top-exterior plane of the absorbent pad to form a channel along the perimeter border. The drawstring system of the absorbent pad includes a drawstring extending within the channel formed along the perimeter border. The drawstring comprises a flexible, continuous string in a loop configuration. The drawstring system may further comprise at least one opening for a section of the drawstring to pass through, and a covering for concealing each one of the at least one openings before use. A user may access the drawstring through at least one opening when one of the coverings is removed.

A method of use is disclosed herein including the following steps: step one, providing an absorbent pad having a planar body including a hydrophilic lining on the top-exterior plane of an absorbent pad, an equivalent hydrophobic lining on a bottom-interior plane of the absorbent pad, a base liner configured to seal the absorbent pad, the base liner extends past a perimeter border of the planar body of the absorbent pad to the top-exterior plane of the absorbent pad and forms a channel along the perimeter border, an adhesive section positioned on the bottom of the base liner, a drawstring system including a drawstring extending within the channel formed along the perimeter border, at least one opening for a section of the drawstring to pass through and allow user access, and a covering for concealing each one of the at least one openings before use; step two, placing and securing the absorbent pad on a surface using the adhesive section; step three, removing a covering and exposing the drawstring; step four, pulling the drawstring and cinching the absorbent pad into a pouch-like configuration; and step five, disposing of the absorbent pad.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, an absorbent pad with drawstring system, constructed and operative according to the teachings of the present disclosure.

The various embodiments of the present invention will hereinafter be described in conjunction with the appended drawings, wherein like designations denote like elements.

DETAILED DESCRIPTION

Figure 1:
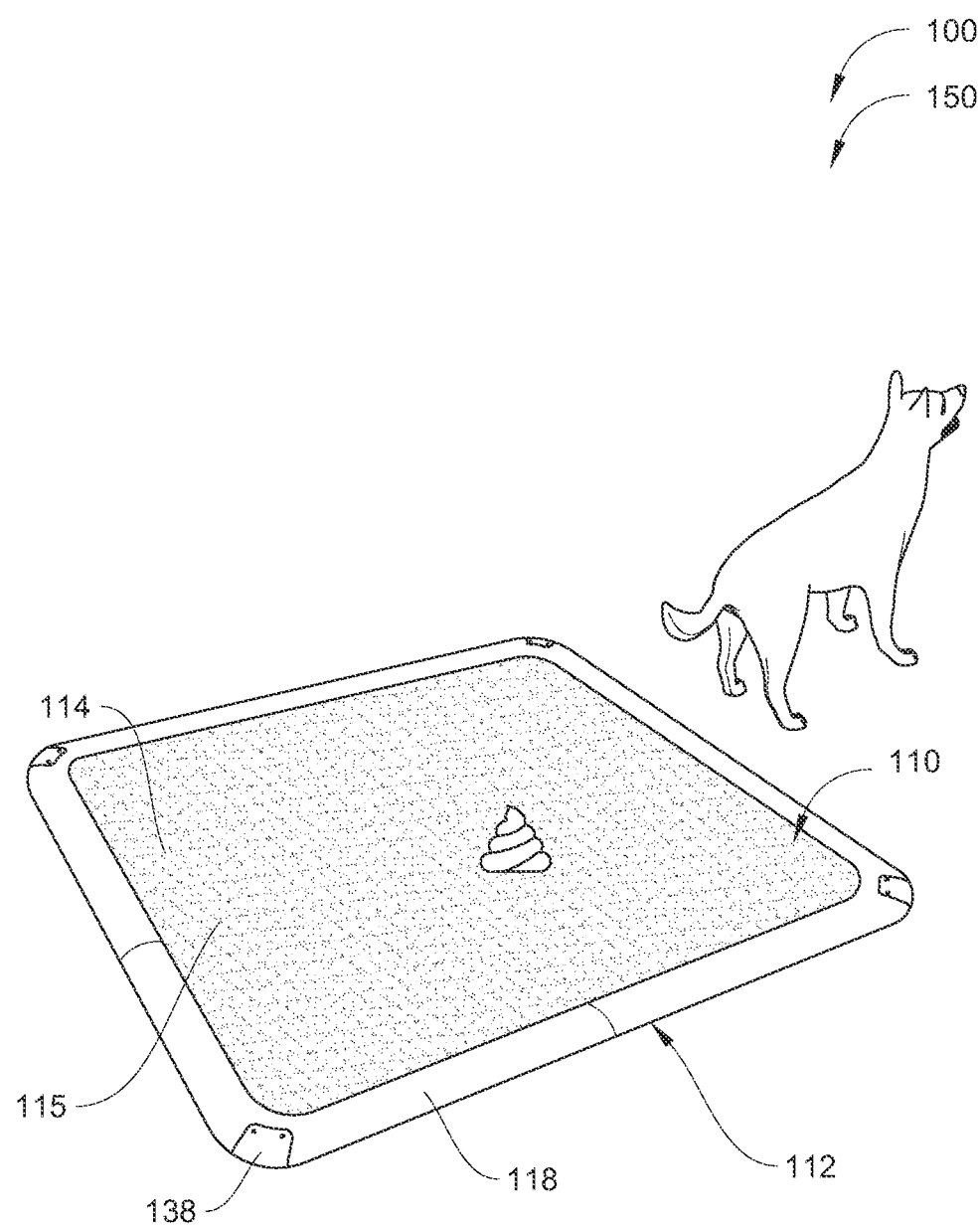
FIG. 1 is a perspective view of the absorbent pad with drawstring system during an 'in-use' condition, according to an embodiment of the disclosure.

As discussed above, embodiments of the present disclosure relate to a pad with drawstrings and more particularly to an absorbent pad with drawstring system as used to improve the collection and disposal of liquid-waste and solid-waste via a novel pad.

Generally, the absorbent pad with drawstring system provides an absorbent pad for use in both professional environments and private households to collect and contain bodily discharges. The absorbent pad is provided for collecting solid-waste and liquid-waste for sanitary containment and disposal of the solid-waste and the liquid-waste. According to a first embodiment, the absorbent pad with drawstring system is provided for medical use. According to a second embodiment, the absorbent pad with drawstring system is provided for pet use.

The absorbent pad includes a planar body made from a super absorbent polymer (SAP) as a base material along with supporting pulp and tissue, including a hydrophilic lining on a top-exterior plane that draws fluid discharges into the absorbent pad, a suitably equivalent hydrophobic lining on a bottom-interior plane that substantially prevents fluid discharges from escaping the absorbent pad, and a base liner configured to further seal the absorbent pad. An adhesive section is positioned on a center portion of the base liner of the absorbent pad for securing and maintaining placement of the absorbent pad on a hosting surface. The base liner extends past a perimeter border of the planar body to the top-exterior plane and forms a channel along the perimeter border. The drawstring system of the absorbent pad includes a drawstring extending within the channel formed along the perimeter border.

The drawstring in preferred embodiments comprises a flexible, continuous string in a loop configuration. The drawstring system further comprises at least one opening for a section of the drawstring to pass through and allows user access. Additionally, the drawstring system comprises at least one covering. The coverings are provided for concealing each one of the at least one openings before use. The coverings disguise the openings and hinder access to the drawstring by small children, uncooperative patients, and pets. Preferably, the absorbent pad features four corners each including an opening and a covering. When a user pulls the drawstring, the four corners of the absorbent pad will draw upward near each other, creating a low-center gravitational point in the absorbent pad and forming a pouch, which further traps in bodily discharge and waste.

In the first embodiment, the absorbent pad with drawstring system can be used with incontinent individuals, both in healthcare and private settings. In the first embodiment, unlike other disposable absorbent pads, the absorbent pad with drawstring system eliminates risks of contact between its collected waste and its patient user and caregiver user. The absorbent pad with drawstring system collects germs, bacteria, and pathogens that are present in collected discharge. The absorbent pad with drawstring system traps the collected discharge and prevents spills thereby preventing the spread of germs that leads to nosocomial infections. By preventing germs, bacteria, and pathogens from spreading to other persons and patients in its environment of use, the absorbent pad with drawstring system helps prevent development of nosocomial infections in medical settings. In the first embodiment, by helping to prevent nosocomial infections, the absorbent pad with drawstring system helps retain the comfort and healing of patients who are already compromised in health and immunity. In the first embodiment, by helping to prevent development of nosocomial infections, the absorbent pad with drawstring system helps improve the healing rate of patients in using environments. In the first embodiment, by helping to prevent development of nosocomial infections, the absorbent pad with drawstring system helps decrease the rate of morbidity of patients in this circumstance. In the first embodiment, by helping to prevent development of nosocomial infections, the absorbent pad with drawstring system addresses a problem that affects ten percent (10%) of all medical facility patients. In the first embodiment, by helping to prevent development of nosocomial infections, the absorbent pad with drawstring system allows using facilities to improve in patient discharge time and patient admissions.

The absorbent pad with drawstring system prevents patients from having continuous contact with fluid discharges. In the first embodiment, by preventing patients from having continuous contact with fluid discharges, the absorbent pad with drawstring system prevents the formation of pressure ulcers, incontinence-associated dermatitis, and other moisture-associated skin damage. In the first embodiment, the absorbent pad with drawstring system prevents absorbed fluid discharges from escaping, both during its use and its disposal. The absorbent pad with drawstring system prevents spills of said fluids onto patients, mattresses, tables, chairs, gurneys, stretchers, floors and other areas.

In the second embodiment, the absorbent pad with drawstring system accepts animal waste on a top-exterior plane. In the second embodiment, the absorbent pad with drawstring system allows animal waste to be collected for disposal and solves a problem suffered by households with indoor dogs. The absorbent pad with drawstring system provides a surface upon which pets can relieve their bladders and bowels while indoors. In the second embodiment, absorbent pad with drawstring system eliminates the risk of dogs relieving themselves on floors, both hard and carpeted, of a residential household and commercial environments such as but not limited to kennels, pet care facilities, breeding facilities, etc. The absorbent pad with drawstring system performs this function in a format that is superior to other devices with similar purposes. In the second embodiment, the absorbent pad with drawstring system eliminates the need to clean up animal waste that otherwise falls from inferior animal waste pads. In the second embodiment, whereas all other animal waste pads need to be rolled or folded by hand, the drawstring of the absorbent pad with drawstring system eliminates those manual formats of pad collection. Further, the absorbent pad eliminates risks of odor left in households.

The absorbent pad with drawstring system prevents collected discharges from escaping during removal from a host surface or structure. In all embodiments, the absorbent pad with drawstring system eliminates labor time for cleaning and sanitizing following spillage from its structure, unlike other absorbent pads.

In a most preferred embodiment, a base liner of the absorbent pad is made of a thin low-density polyethylene (LDPE) material that measures approximately twenty-six inches in width by twenty-seven inches in length (26"×27"). Applied to a center of the base liner is a layered pad, measuring approximately twenty-three inches in width by twenty-four inches in length (23"×24"). The absorbent pad includes super absorbent polymer (SAP) as the base material, along with supporting pulp and tissue. A hydrophilic lining is featured on a top-exterior plane of the pad and a hydrophobic lining is included on a bottom-interior plane. The absorbent pad is centered on, and applied by adhesive upon, the base liner. The remaining one and one-half inches (1½") of the base liner are then folded over, and one inch (1") of this flap is adhesively applied to the absorbent pad to form a border. The remaining half-inch (½") forms an open channel in the folded portion of the base liner. A drawstring, made of a light and durable plastic material, occupies the open channel. At each corner of the absorbent pad with drawstring system a portion of the overlapping base liner is perforated, forming a sealed cover, configured to only allow access to the drawstring when needed. Located on the bottom plane of absorbent pad with drawstring system is at least one tab of pressure-sensitive adhesive (PSA), which is used to maintain placement of the pad on the hosting surface. The PSA is covered and protected by a wax paper coating until time of use.

The absorbent pad of the absorbent pad with drawstring system can include a various number of layers, and which can be made of various suitable materials, including but not limited to wood pulp, tissue paper, cotton material, bamboo, plastic film, and various super absorbent polymers (SAP). The absorbent pad of the absorbent pad with drawstring system may or may not include various gelatins and/or polymers, including but not limited to sodium polyacrylate and coal, and with purpose of containing any collected urine, blood or other liquid-like discharge as a dense, solid material. The absorbent pad with drawstring system may or may not include a hydrophilic lining and/or a hydrophobic lining.

In one embodiment a method of use may be as follows: a user may remove a removable covering protecting the adhesive section and then lay the absorbent pad with drawstring system on a top surface of any structure used for hosting patients, including but not limited to hospital beds, residential beds, surgical tables, stretchers, gurneys, examination chairs and examination tables. Should a patient lying on absorbent pad with drawstring system relieve themselves or discharge any other bodily fluids, the discharge will be drawn within the absorbent pad by the hydrophobic lining on the top-exterior plane of the absorbent pad. The discharge will also be effectively prevented from escaping by the hydrophobic lining on the bottom-interior plane of the absorbent pad. When the absorbent pad has collected any liquid, solid or semisolid waste, and after the patient has been removed from the absorbent pad, a caregiving user may tear back a covering to reveal the drawstring. The user may then pull on the drawstring, raising up all sides of the absorbent pad with drawstring system and forming a pouch. The user may continue pulling on the drawstring until the pouch is fully formed, thus sealing all discharge that may have been deposited on the absorbent pad with drawstring system by the patient. The user may then safely dispose of the absorbent pad with drawstring system without any of its collected waste escaping.

In another embodiment a method of use may be as follows: a pet owner can remove the removable covering protecting the adhesive section and then lay the pad on a floor surface. After a pet uses the absorbent pad for bladder and/or bowel relief, the pet owner can simply tear back a covering to reveal the drawstring. The user may then pull on the drawstring, raising up all sides of the absorbent pad with drawstring system and forming a pouch. The user may continue pulling on the drawstring until the pouch is fully formed, thus sealing all urine and feces that may have been deposited by the pet. The pet owner may then dispose of the absorbent pad without risk of hand contact with pet waste, without spills, and without a need to clean up after pet waste spills.

Referring now more specifically to the drawings by numerals of reference, there is shown in FIGS. 1-9, various views of an absorbent pad with drawstring system 100.

FIG. 1 shows an absorbent pad with drawstring system 100 during an 'in-use' condition 150, according to an embodiment of the present disclosure. In one embodiment, the absorbent pad with drawstring system 100 allows common sanitation duties in healthcare to be conducted easier, faster, and safer. In a second embodiment, the absorbent pad with drawstring system 100 offers significant improvement to a common and undesirable pet-care task. As illustrated, the absorbent pad with drawstring system 100 may include an absorbent pad 110 having a drawstring system 130. The absorbent pad 110 comprises a planar body 112 including a hydrophilic lining 114 on a top-exterior plane 115, a hydrophobic lining 116 on a bottom-interior plane 117, and a base liner configured to seal the bottom-interior plane 117. The base liner 118 comprises a plastic, waterproof material. The absorbent pad 110 is provided for collecting waste including solid-waste and liquid-waste for sanitary containment and disposal of the solid-waste and the liquid-waste.

Figure 2:
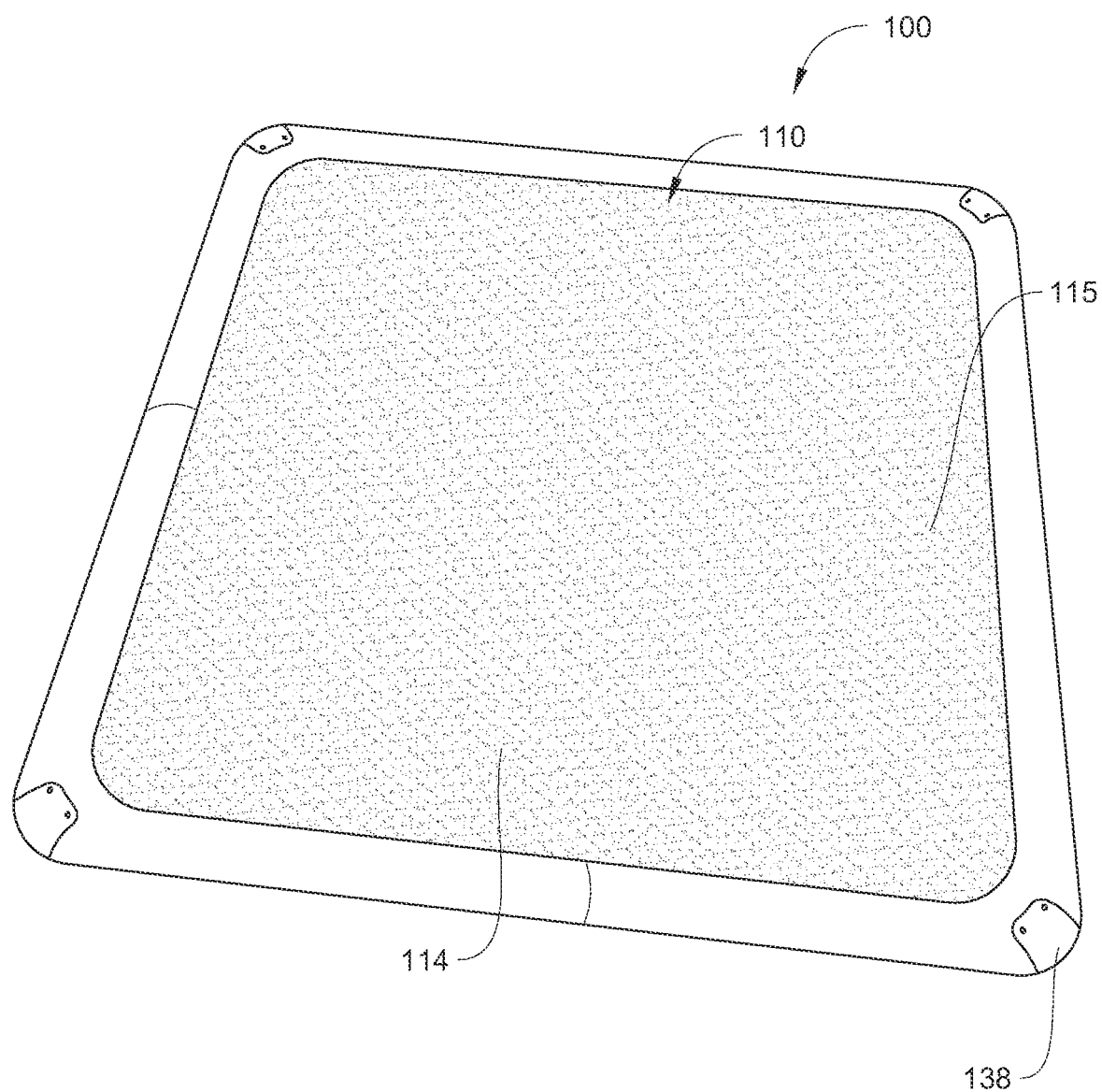
FIG. 2 is a top perspective view of the absorbent pad with drawstring system of FIG. 1 including an absorbent pad having a drawstring system, according to an embodiment of the present disclosure.

FIG. 2 is a top perspective view of the absorbent pad with drawstring system 100 of FIG. 1 including the absorbent pad 110 having the drawstring system 130, according to an embodiment of the present disclosure. The absorbent pad 110 has a planar body 112 comprising a plurality of layers. The planar body 112 may include the hydrophilic lining 114 on the top-exterior plane 115, the hydrophobic lining 116 on the bottom-interior plane 117, and the base liner 118 configured to seal the absorbent pad 110. As shown, the base liner 118 extends past a perimeter border 122 of the planar body 112 to the top-exterior plane 115 and forms a channel 120 along the perimeter border 122. The drawstring system 130 of the absorbent pad 110 includes a drawstring 132 extending within the channel 120 formed along the perimeter border 122. The drawstring 132 comprises a flexible, continuous string in a loop configuration. The drawstring system 130 further comprises at least one opening 136 for a section of the drawstring 132 to pass through and allow user access and a covering 138. The covering 138 is provided for concealing each one of the at least one openings 136 before use.

Figure 3:
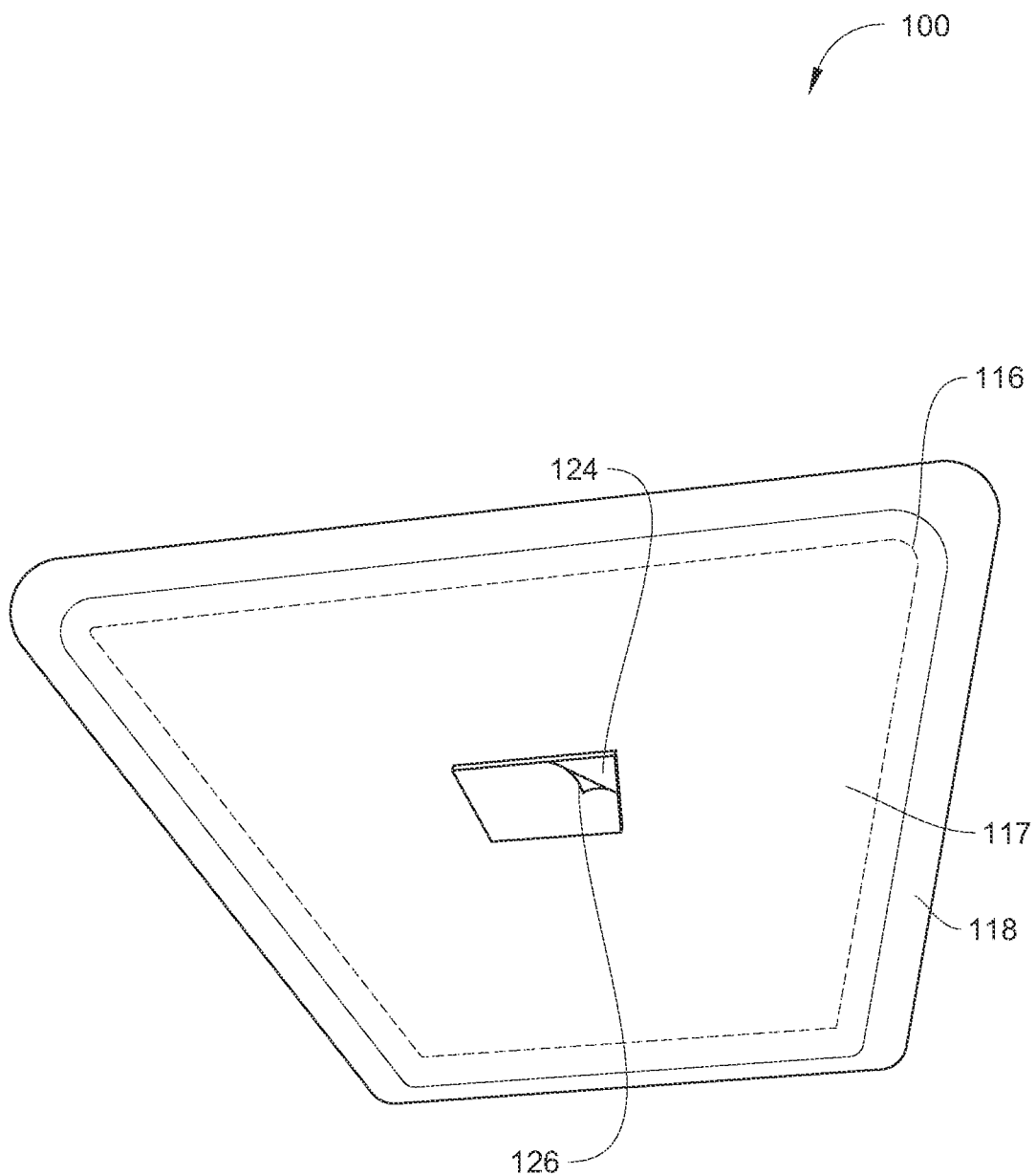
FIG. 3 is a bottom perspective view of the absorbent pad having an adhesive section, according to an embodiment of the present disclosure.

FIG. 3 is a bottom perspective view of the absorbent pad 110 having an adhesive section 124, according to an embodiment of the present disclosure. The absorbent pad 110 of the absorbent pad with drawstring system 100 may comprise a generally square or rectangular profile. In one embodiment, the absorbent pad 110 comprises a width of approximately 26 inches and a length of approximately 27 inches. The absorbent pad 110 may be provided in various sizes and shapes, including specific sizes and shapes intended for specific places of application. The adhesive section 124 is positioned on the base liner 118 of the absorbent pad 110. The adhesive section 124 may include at least one tab of pressure-sensitive adhesive and is configured to maintain placement of the absorbent pad 110 on a hosting surface. The adhesive section 124 may be positioned at a center point of the base liner 118. In a preferred embodiment, the adhesive section 124 includes a removable covering 126 for concealing the at least one tab of pressure-sensitive adhesive before use. The absorbent pad with drawstring system 100 is easily removable from a host surface or structure when needed. By folding up and closing with use of the drawstring system 130, the absorbent pad with drawstring system 100 covers and encloses any material collected within and/or upon the absorbent pad 110.

Figure 4:
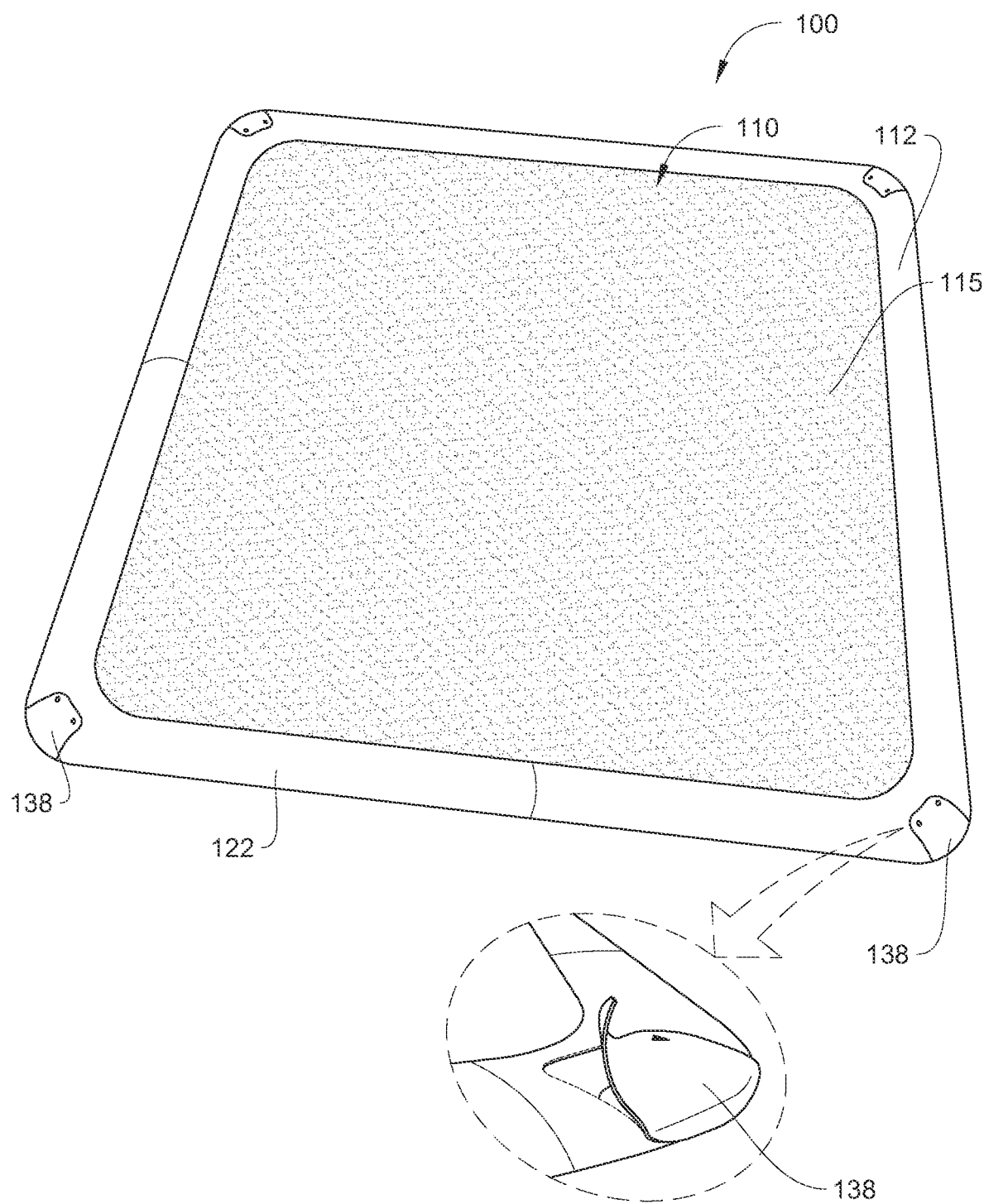
FIG. 4 is a perspective view of the absorbent pad of FIG. 1 comprising a drawstring system including a drawstring, at least one opening, and a covering for concealing each one of the at least one openings, according to an embodiment of the present disclosure.

FIG. 4 is a perspective view of the absorbent pad 110 of FIG. 1 comprising the drawstring system 130 including the drawstring 132, the at least one opening 136, and the covering 138 for concealing each one of the at least one openings 136, according to an embodiment of the present disclosure. In one embodiment, the drawstring system 130 includes four of the at least one openings 136. The at least one openings 136 may be positioned at opposing corners of the absorbent pad 110. In this embodiment, four of the coverings 138 are provided for concealing each one of the at least one openings 136 before use. The covering 138 may be a removable perforated tab or other removable section.

Figure 5:
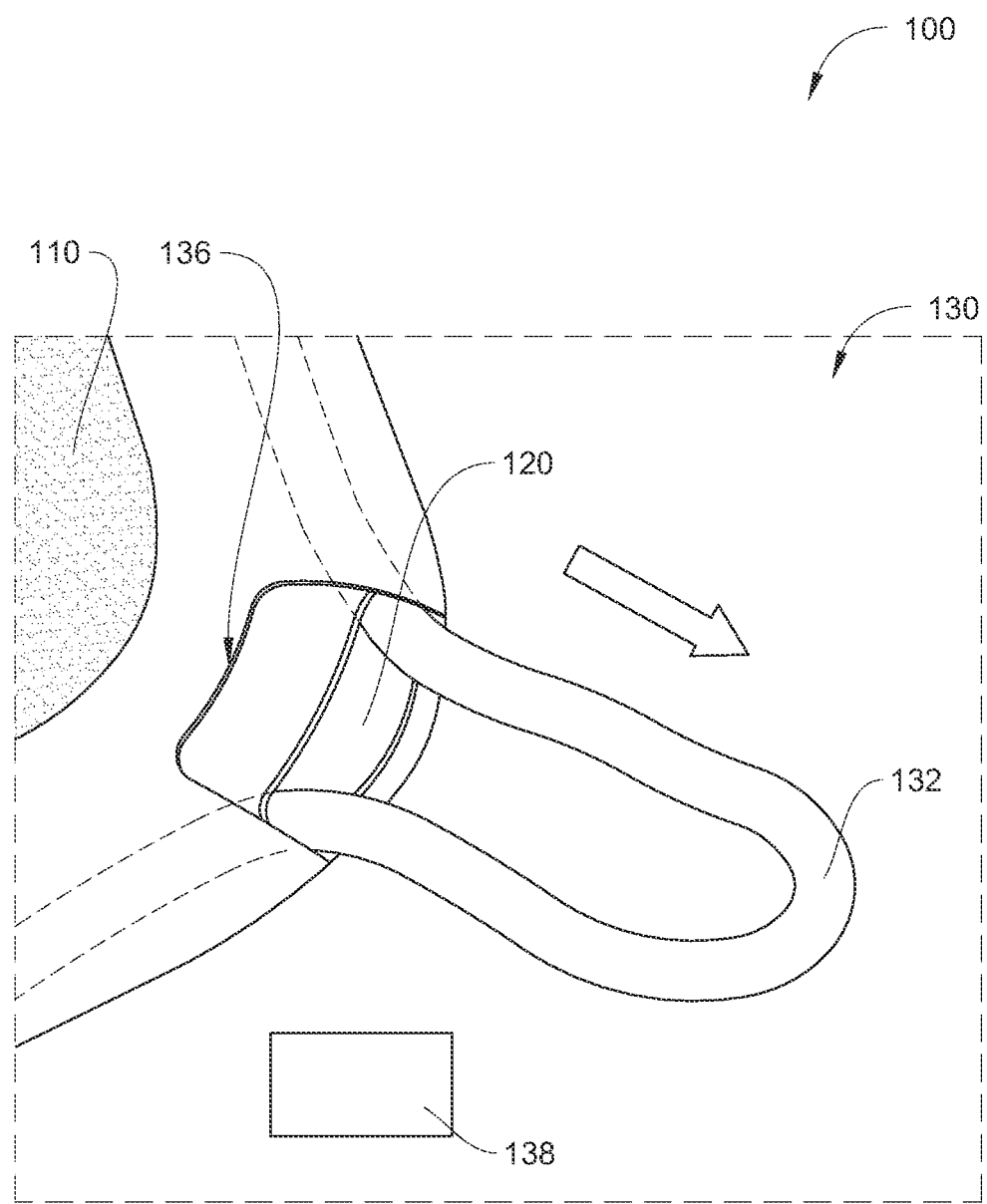
FIG. 5 is a perspective view of the drawstring system including the drawstring extending through the at least one opening, according to an embodiment of the present disclosure.

FIG. 5 is a perspective view of the drawstring system 130 including the drawstring 132 extending through the at least one opening 136, according to an embodiment of the present disclosure. The absorbent pad 110 includes a plurality of layers for absorbing and containing liquid-waste and solid-waste for disposal. The absorbent pad 110 of the absorbent pad with drawstring system 100 may include a various number of layers, and which can be made of various suitable materials, including but not limited to wood pulp, tissue paper, cotton material, bamboo, plastic film, and various superabsorbent polymers (SAP). The absorbent pad 110 of the absorbent pad with drawstring system 100 may or may not include various gelatins and/or polymers, including but not limited to sodium polyacrylate and coal, and with purpose of containing any collected urine, blood or other liquid-like discharge as a dense, solid material. The absorbent pad with drawstring system 100 may or may not include a hydrophilic lining 114 and/or a hydrophobic lining 116. The base liner 118 may be made of any applicable material, including but not limited to low-density polyethylene (LDPE) and polyvinyl chloride (PVC). Segments of frictional and/or adhesive material may also be included with purpose of preventing the absorbent pad 110 from sliding on the hosting surface.

Figure 6:
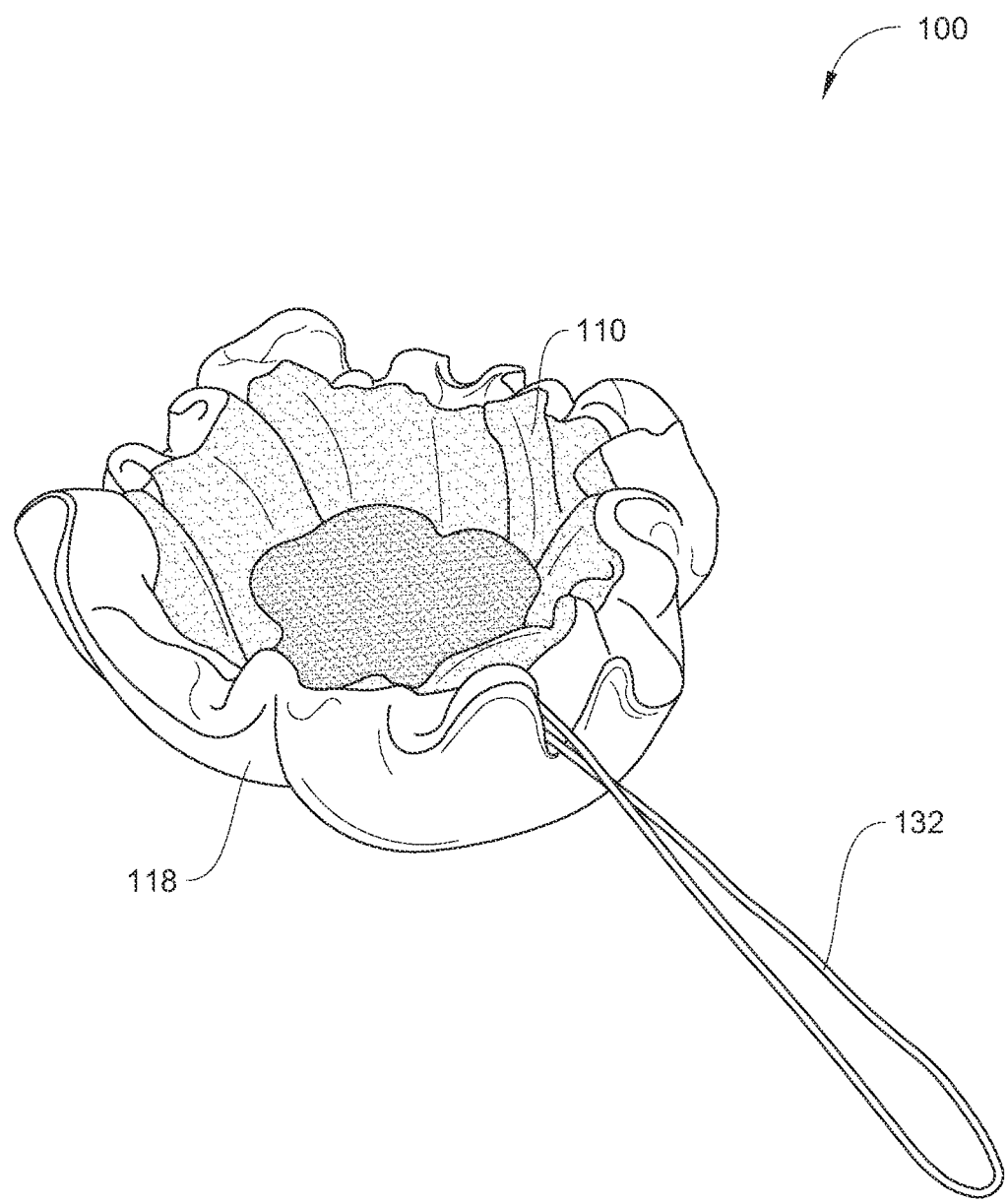
FIG. 6 is a perspective view of the absorbent pad with drawstring system of FIG. 1 in a cinching condition with the drawstring of the absorbent pad being exposed, according to an embodiment of the present disclosure.

FIG. 6 is a perspective view of the absorbent pad with drawstring system 100 of FIG. 1 in a cinching condition with the drawstring 132 of the absorbent pad 110 being exposed, according to an embodiment of the present disclosure. The drawstring 132 comprises a flexible, continuous string in a loop configuration. Pulling of the drawstring 132 causes the absorbent pad 110 to form a pouch and conceal the solid-waste collected on the absorbent pad 110 for disposal. In certain embodiments, the absorbent pad 110 may be infused with a sanitizing agent and/or an odor eliminating fragrance, super absorbent gel materials, and/or reactive agents that indicate use by color change. Super absorbent polymers may include sodium polyacrylate and/or potassium polyacrylate. Odor eliminating fragrances may include eucalyptus, lavender, pine, cedar, and the like. Sanitizing agent may include sodium hypochlorite, hydrogen peroxide, alcohol. In an embodiment for use with pets, the absorbent pad 110 may be treated with various ammonias and/or pheromones to promote desired use and intention of the absorbent pad 110.

Figure 7:
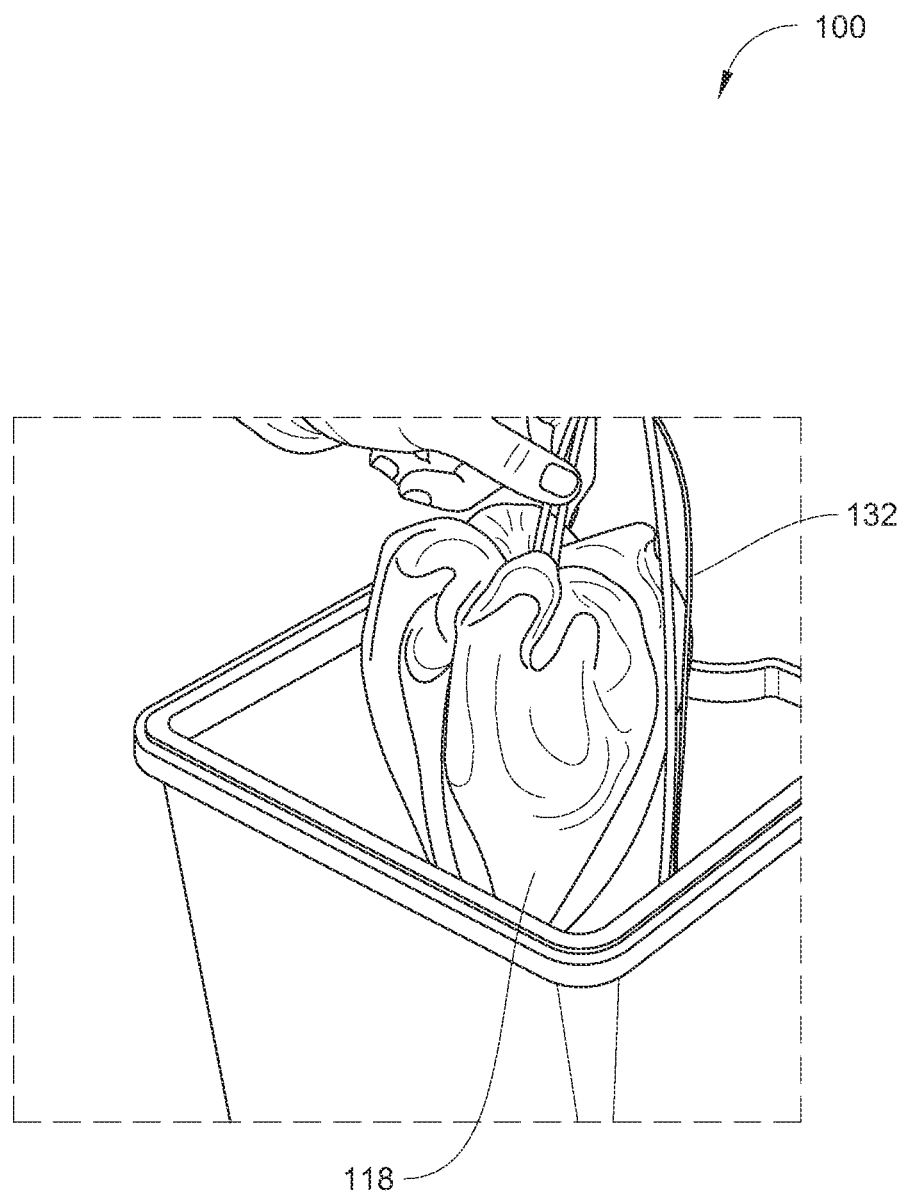
FIG. 7 is a perspective view of the absorbent pad with drawstring system of FIG. 1 in a fully cinched condition for disposal, according to an embodiment of the present disclosure.

FIG. 7 is a perspective view of the absorbent pad with drawstring system 100 of FIG. 1 in a fully cinched condition for disposal, according to an embodiment of the present disclosure. The absorbent pad 110 is disposable and provides sanitary means for collecting and disposing of solid-waste and liquid-waste.

Figure 8:
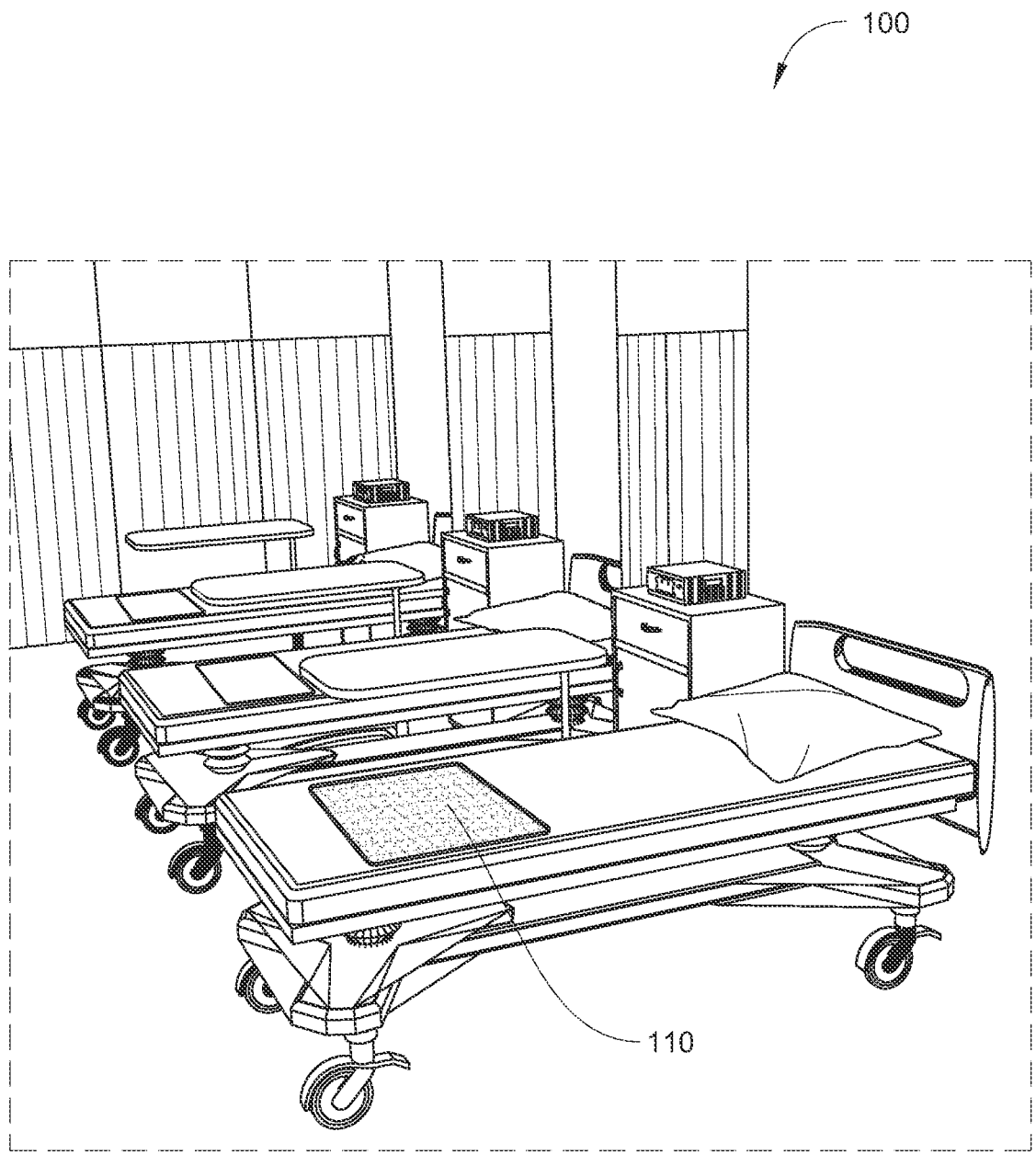
FIG. 8 is a perspective view of the absorbent pad with drawstring system during an 'in-use' condition, according to an alternative embodiment of the disclosure.

FIG. 8 is a perspective view of the absorbent pad with drawstring system 100 during an 'in-use' condition, according to an alternative embodiment of the disclosure. As shown, the absorbent pad 110 may be provided for use upon hospital beds, residential beds, gurneys, stretchers, surgical tables, examination chairs and examination tables and other patient-hosting surfaces. When the absorbent pad 110 has collected any liquid-waste, solid-waste or semisolid-waste, a user may simply tear back one of the coverings 138 to reveal the drawstring 132. The user may then pull on the drawstring 132, raising up all sides of the absorbent pad with drawstring system 100 and forming a pouch. The user may continue pulling on the drawstring 132 until the pouch is fully formed, thus sealing all discharge that may have been deposited on the absorbent pad 110. The user may then safely dispose of absorbent pad 110 without any collected waste escaping. With use of the drawstring 132, a used absorbent pad with drawstring system 100 can be collected, closed, and sealed, eliminating any risks of spillage of any bodily fluids or materials it contains. Absorbent pad with drawstring system 100 also eliminates any risk of caregiver contact with any bodily fluids it effectively contains.

Figure 9:
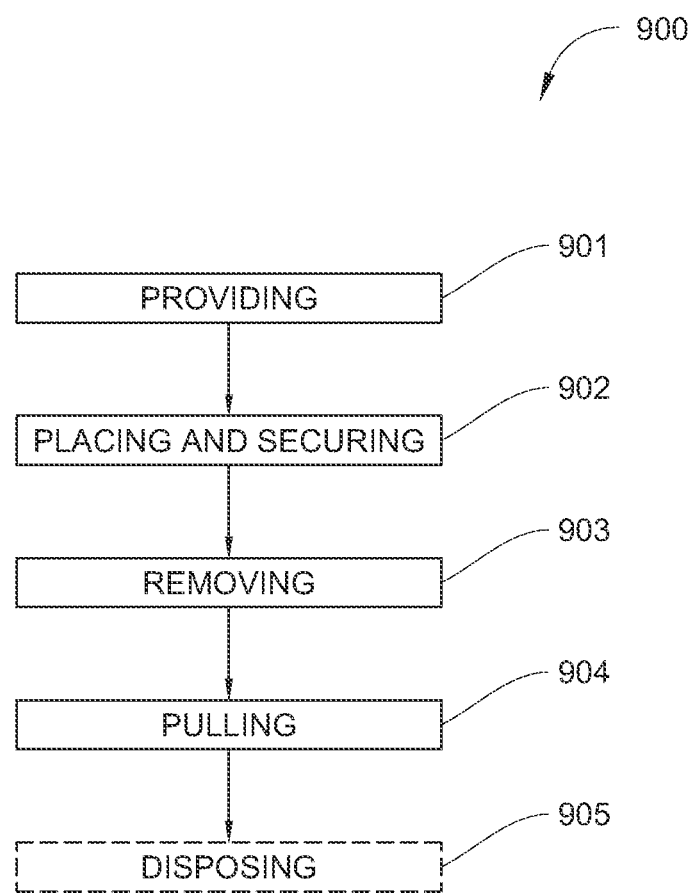
FIG. 9 is a flow diagram illustrating a method for using an absorbent pad with drawstring system, according to an embodiment of the present disclosure.

FIG. 9 is a flow diagram illustrating a method for using an absorbent pad with drawstring system, according to an embodiment of the present disclosure. In particular, the method for using an absorbent pad with drawstring system 900 may include one or more components or features of the absorbent pad with drawstring system 100 as described above. As illustrated, the method for using an absorbent pad with drawstring system 900 may include the steps of: step one 901, providing an absorbent pad 110 having a planar body 112 including a hydrophilic lining 114 on a top-exterior plane 115, a hydrophobic lining 116 on a bottom-interior plane 117, a base liner 118 configured to seal the absorbent pad 110, the base liner 118 extends past a perimeter border 122 of the planar body 112 to the top-exterior plane and forms a channel 120 along the perimeter border 122, an adhesive section 124 positioned on the base liner 118, a drawstring system 130 including a drawstring 132 extending within the channel 120 formed along the perimeter border 122, at least one opening 136 for a section of the drawstring 132 to pass through and allow user access, and a covering 138 for concealing each one of the at least one openings 136 before use; step two 902, placing and securing the absorbent pad 110 on a surface using the adhesive section 124; step three 903, removing a covering 138 and exposing the drawstring 132; step four 904, pulling the drawstring 132 and cinching the absorbent pad 110 into a pouch-like configuration; and step five 905, disposing of the absorbent pad 110.

It should be noted that step five 905 is an optional step and may not be implemented in all cases. Optional steps of method of use 900 are illustrated using dotted lines in FIG. 9 so as to distinguish them from the other steps of method of use 900. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for using an absorbent pad with drawstring system, are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A method of using an absorbent pad with drawstring system to collect and dispose of waste said method comprising:
   providing an absorbent pad having,
      a planar body including,
         a hydrophilic lining on a top-exterior plane,
         a hydrophobic lining on a bottom-interior plane,
         a base liner configured to seal said absorbent pad, said base liner extends past a perimeter border of said planar body to said top-exterior plane and forms a channel along said perimeter border,
         a tab of pressure sensitive adhesive positioned at a center point of said base liner,
         a removable covering configured over said tab of pressure sensitive adhesive
         a drawstring system including,
            a drawstring extending within said channel formed along said perimeter border,
            an opening in the channel for a section of said drawstring to pass through, and
            a covering for concealing said opening before use;
   removing the removable covering from the pressure sensitive adhesive section;
   placing and securing said absorbent pad on a surface using said tab of pressure sensitive adhesive to secure and maintain placement of the absorbent pad on said surface;
   collecting at least one of a solid-waste or a liquid-waste onto said absorbent pad;
   removing said covering and exposing said drawstring;
   pulling said drawstring to raise up the perimeter border of the absorbent pad while secured to said surface by said tab of pressure sensitive adhesive to cinch said absorbent pad into a pouch with said solid-waste or said liquid waste configured in said pouch;
   detaching the pressure sensitive adhesive from the surface;
   picking up the absorbent pad from said surface, and
   disposing of the absorbent pad after picking up the absorbent pad from said surface.

2. An absorbent pad with drawstring system, the absorbent pad with drawstring system consisting of:
   an absorbent pad having,
      a planar body including, a super absorbent polymer (SAP) as a base material, along with supporting pulp and tissue;
a hydrophilic lining on a top-exterior plane;
a hydrophobic lining on a bottom-interior plane,
a base liner configured to seal said absorbent pad, said base liner extends past a perimeter border of said planar body to said top-exterior plane and forms a channel along said perimeter border,
a pressure sensitive adhesive section positioned at a center point of on said base liner,
a drawstring system including,
a drawstring extending within said channel formed along said perimeter border,
an opening in the channel for a section of said drawstring to pass through and allow user access, and
a covering for concealing said opening before use,
wherein said absorbent pad is provided for collecting solid-waste and liquid-waste for sanitary containment and disposal of said solid-waste and said liquid-waste;
wherein said adhesive section comprises a tab of pressure-sensitive adhesive and is configured to maintain placement of said absorbent pad on a hosting surface;
wherein said absorbent pad is disposable;
wherein said absorbent pad comprises a plurality of layers;
wherein said absorbent pad is infused with a sanitizing agent; and
wherein said absorbent pad is infused with an odor eliminating fragrance.

* * * * *